(12) United States Patent
Boyer et al.

(10) Patent No.: US 9,220,509 B2
(45) Date of Patent: Dec. 29, 2015

(54) ADJUSTABLE GUIDE IN COMPUTER ASSISTED ORTHOPAEDIC SURGERY

(75) Inventors: Anthony Boyer, Echirolles (FR); Stéphane Lavallee, St Martin d'Uriage (FR)

(73) Assignee: BLUE ORTHO, La Tronche (FR)

( * ) Notice: Subject to any disclaimer, the term of this patent is extended or adjusted under 35 U.S.C. 154(b) by 974 days.

(21) Appl. No.: 13/381,615

(22) PCT Filed: Jun. 29, 2010

(86) PCT No.: PCT/IB2010/001938
§ 371 (c)(1),
(2), (4) Date: Feb. 22, 2012

(87) PCT Pub. No.: WO2011/001292
PCT Pub. Date: Jan. 6, 2011

(65) Prior Publication Data
US 2012/0143198 A1    Jun. 7, 2012

Related U.S. Application Data

(60) Provisional application No. 61/221,639, filed on Jun. 30, 2009.

(51) Int. Cl.
*A61B 17/56* (2006.01)
*A61B 17/15* (2006.01)
(Continued)

(52) U.S. Cl.
CPC ............... *A61B 17/15* (2013.01); *A61B 17/151* (2013.01); *A61B 17/152* (2013.01);
(Continued)

(58) Field of Classification Search
CPC .... A61B 17/15; A61B 17/151; A61B 17/152; A61B 17/154; A61B 17/155; A61B 17/157
See application file for complete search history.

(56) References Cited

U.S. PATENT DOCUMENTS 4,457,307 A * 7/1984 Stillwell .......................... 606/88
4,681,843 A * 7/1987 Egerer et al. .................... 435/41
(Continued)

FOREIGN PATENT DOCUMENTS

DE    100 29 737    5/2003
EP    0 728 446    8/1996
(Continued)

OTHER PUBLICATIONS

International Search Report and Written Opinion Based on PCT/IB2010/001804 mailed Feb. 8, 2011.
(Continued)

*Primary Examiner* — Christian Sevilla
(74) *Attorney, Agent, or Firm* — Miles & Stockbridge PC

(57) ABSTRACT

The present invention relates to a surgical navigation device, for the purpose of adjusting cutting planes to a desired position with respect to a bone of a patient, the device comprising:
  an adjustable guide (15) that contains several adjustable screws (1) that create contact points with the surface of the bone or cartilage such that the guide fits to the bone in a unique position calculated such that the holes and cutting blocks of the adjustable guide fit with the position planned on preoperative CT or MR images of the patient,
  a dedicated screwdriver (7) to adjust automatically the screws (1) to their target length,
  a navigation system used to check the correct position of the adjustable guide with respect to essential anatomical points and if necessary means to correct the positions of the adjustable screws.

15 Claims, 8 Drawing Sheets

(51) Int. Cl.
  *A61B 17/88* (2006.01)
  *A61B 19/00* (2006.01)
  *A61B 17/00* (2006.01)

(52) U.S. Cl.
  CPC ............ *A61B 17/154* (2013.01); *A61B 17/155* (2013.01); *A61B 17/157* (2013.01); *A61B 17/8875* (2013.01); *A61B 19/50* (2013.01); *A61B 19/5244* (2013.01); *A61B 2017/00398* (2013.01); *A61B 2019/462* (2013.01); *A61B 2019/508* (2013.01)

(56) References Cited

U.S. PATENT DOCUMENTS

| | | | | |
|---|---|---|---|---|
| 4,703,751 | A * | 11/1987 | Pohl | 606/62 |
| 4,706,665 | A * | 11/1987 | Gouda | 606/130 |
| 5,251,127 | A * | 10/1993 | Raab | 606/130 |
| 5,305,203 | A * | 4/1994 | Raab | 606/1 |
| 5,364,402 | A * | 11/1994 | Mumme et al. | 606/88 |
| 5,514,139 | A * | 5/1996 | Goldstein et al. | 606/79 |
| 5,682,886 | A * | 11/1997 | Delp et al. | 600/407 |
| 5,797,918 | A * | 8/1998 | McGuire et al. | 606/104 |
| 5,806,518 | A * | 9/1998 | Mittelstadt | 600/407 |
| 5,871,018 | A | 2/1999 | Delp et al. | |
| 5,995,738 | A * | 11/1999 | DiGioia et al. | 703/11 |
| 6,077,270 | A * | 6/2000 | Katz | 606/88 |
| 6,340,363 | B1 * | 1/2002 | Bolger et al. | 606/90 |
| 6,351,659 | B1 * | 2/2002 | Vilsmeier | 600/407 |
| 6,450,978 | B1 * | 9/2002 | Brosseau et al. | 600/595 |
| 6,533,737 | B1 * | 3/2003 | Brosseau et al. | 600/595 |
| 6,551,325 | B2 * | 4/2003 | Neubauer et al. | 606/88 |
| 6,685,711 | B2 * | 2/2004 | Axelson et al. | 606/88 |
| 6,712,824 | B2 * | 3/2004 | Millard et al. | 606/87 |
| 6,991,655 | B2 * | 1/2006 | Iversen | 623/22.12 |
| 7,029,477 | B2 * | 4/2006 | Grimm | 606/88 |
| 7,419,492 | B2 * | 9/2008 | Yoon et al. | 606/91 |
| 2002/0010465 | A1 | 1/2002 | Koo et al. | |
| 2002/0133160 | A1 * | 9/2002 | Axelson et al. | 606/88 |
| 2003/0181800 | A1 * | 9/2003 | Bonutti | 600/407 |
| 2004/0044295 | A1 * | 3/2004 | Reinert et al. | 600/587 |
| 2004/0092944 | A1 | 5/2004 | Penenberg | |
| 2004/0097952 | A1 * | 5/2004 | Sarin et al. | 606/102 |
| 2004/0143340 | A1 * | 7/2004 | Tuma et al. | 623/22.12 |
| 2004/0230199 | A1 * | 11/2004 | Jansen et al. | 606/91 |
| 2004/0243148 | A1 * | 12/2004 | Wasielewski | 606/130 |
| 2004/0254584 | A1 * | 12/2004 | Sarin et al. | 606/102 |
| 2005/0010299 | A1 * | 1/2005 | Disilvestro | 623/18.12 |
| 2005/0010301 | A1 * | 1/2005 | Disilvestro et al. | 623/18.12 |
| 2005/0021044 | A1 * | 1/2005 | Stone et al. | 606/102 |
| 2005/0065617 | A1 * | 3/2005 | Moctezuma de la Barrera et al. | 623/908 |
| 2005/0119661 | A1 * | 6/2005 | Hodgson et al. | 606/90 |
| 2005/0203536 | A1 * | 9/2005 | Laffargue et al. | 606/91 |
| 2005/0234466 | A1 * | 10/2005 | Stallings | 606/88 |
| 2005/0234468 | A1 * | 10/2005 | Carson | 606/96 |
| 2006/0036257 | A1 * | 2/2006 | Steffensmeier | 606/90 |
| 2006/0122617 | A1 * | 6/2006 | Lavallee et al. | 606/87 |
| 2006/0195111 | A1 * | 8/2006 | Couture | 606/86 |
| 2006/0200161 | A1 * | 9/2006 | Plaskos et al. | 606/88 |
| 2006/0217733 | A1 * | 9/2006 | Plassky et al. | 606/87 |
| 2006/0235290 | A1 * | 10/2006 | Gabriel et al. | 600/407 |
| 2007/0010258 | A1 * | 1/2007 | Landschaft et al. | 455/456.1 |
| 2007/0038223 | A1 * | 2/2007 | Marquart et al. | 606/86 |
| 2007/0055289 | A1 * | 3/2007 | Scouten et al. | 606/130 |
| 2007/0055389 | A1 * | 3/2007 | Harwood | 700/19 |
| 2007/0066917 | A1 * | 3/2007 | Hodorek et al. | 600/595 |
| 2007/0162142 | A1 * | 7/2007 | Stone | 623/20.14 |
| 2007/0179626 | A1 * | 8/2007 | de la Barrera et al. | 623/20.14 |
| 2007/0219561 | A1 * | 9/2007 | Lavallee et al. | 606/90 |
| 2007/0244488 | A1 * | 10/2007 | Metzger et al. | 606/90 |
| 2008/0009952 | A1 * | 1/2008 | Hodge | 623/22.21 |
| 2008/0071195 | A1 * | 3/2008 | Cuellar et al. | 600/595 |
| 2008/0146969 | A1 * | 6/2008 | Kurtz | 600/595 |
| 2008/0214960 | A1 * | 9/2008 | Hodgson et al. | 600/587 |
| 2008/0275452 | A1 * | 11/2008 | Lang et al. | 606/88 |
| 2008/0287954 | A1 * | 11/2008 | Kunz et al. | 606/87 |
| 2008/0319491 | A1 * | 12/2008 | Schoenefeld | 606/86 R |
| 2009/0005783 | A1 * | 1/2009 | Gotte et al. | 606/87 |
| 2012/0053591 | A1 * | 3/2012 | Haines et al. | 606/88 |
| 2013/0144302 | A1 * | 6/2013 | Reeve | 606/102 |

FOREIGN PATENT DOCUMENTS

| | | |
|---|---|---|
| EP | 1 226 778 | 7/2002 |
| EP | 1 245 193 | 10/2002 |
| EP | 1 430 842 | 6/2004 |
| EP | 1 444 957 | 8/2004 |
| EP | 1 574 170 | 9/2005 |
| EP | 1 665 992 | 6/2006 |
| EP | 1 669 033 | 6/2006 |
| EP | 1 679 047 | 7/2006 |
| EP | 1 707 159 | 10/2006 |
| EP | 2 042 110 | 4/2009 |
| FR | 2 856 268 | 12/2004 |
| WO | 01/78015 | 10/2001 |
| WO | 02/37935 | 5/2002 |
| WO | 03/009768 | 2/2003 |
| WO | 03/079940 | 10/2003 |
| WO | 2009/105479 | 8/2009 |
| WO | 2009/127404 | 10/2009 |
| WO | 2010/125474 | 11/2010 |

OTHER PUBLICATIONS

International Preliminary Report on Patentability and Written Opinion Based on International Application No. PCT/EP2009/063930 Issued Apr. 26, 2011.
Kosmopoulos, PH.D. et al; "Pedicle Screw Placement Accuracy: A Meta-Analysis", Spine; 2007; vol. 32, No. 3; pp. E111-E120; Lippincott Williams & Wilkins, Inc.
Grützner et al.; "Klinische Studie Zur Registrierungsfreien 3D-Navigation Mit Dem Mobilen C-Bogen Siremobil ISO-C 3D"; Electromedica; 2003; vol. 71; No. 1; pp. 58-67; Lippincott Williams & Wilkins, Inc.
Schaeren et al; "Effektive In-Vivo-Strahlendosis Bei Bildwandlerkrontollierter Pedikelinstrumentation vs. CT-Basierter Navigation"; Orthopade; Apr. 2002; vol. 31, No. 4; pp. 392-396; Springer-Verlag.
Laine et al.; "Accuracy of Pedicle Screw Insertion With and Without Computer Assistance: A Randomised Controlled Clinical Study in 100 Consecutive Patients"; European Spine Journal; 2000; vol. 9; No. 3; pp. 235-240; Springer-Verlag.
Sukovich et al; "Miniature Robotic Guidance for Pedicle Screw Placement in Posterior Spinal Fusion: Early Clinical Experience With the Spineassist"; International Journal of Medical Robotics and Computer Assisted Surgeryr+; Jun. 2006; vol. 2, No. 2; pp. 114-122; John Wiley & Sons, Ltd.
Wendl et al; "ISO-C3D-Gestutzte Navigierte Implantation Von Pedikiel-Schrauben an BWS und LWS"; Unfallchirurg; Nov. 2003; vol. 106; No. 11; pp. 907-913; Springer-Verlag.
Susil et al.; "A Single Image Registration Method for CT Guided Interventions" MICCAI '99; 1999; LNCS 1679; pp. 798-808; Springer-Verlag Berlin Heidelberg.
Amiot et al.; "Comparative Results Between Conventional and Computer-Assisted Pedicle Screw Installation in the Thoracic, Lumbar, and Sacral Spine"; Spine; 2000; vol. 25; No. 5; pp. 606-614; Lippincott Williams & Wilkins, Inc.
Hamadeh et al.; "Automated 3-Dimensional Computed Tomographic and Fluoroscopic Image Registration"; 1998; Computer Aided Surgery; Biomedical Paper; vol. 3; No. 1; pp. 11-19; Wiley-Liss, Inc.
Horn; "Closed-Form Solution of Absolute Orientation Using Unit Quaternions"; 1987; Journal of the Optical Society of America A; 1987; vol. 4; p. 629; Optical Society of America.
Merloz et al.; "Computer-Assisted Spine Surgery"; 1998; Computer Aided Surgery; vol. 3; pp. 297-305; Wiley-Liss, Inc.
Lazovic; "Cup and Stem Navigation With the Orthopilot System, In Navigation and Mis in Orthopaedic Surgery"; 2007; Ed. Stiehl JB; Konermann WH, Haaker RG, Digioia AM; Springer Medizin Verlag; Heidelberg; pp. 372-378.

(56) References Cited

OTHER PUBLICATIONS

Perlick et al.; "Cup and Stem Navigated With the Vector Vision System. In Navigation and Mis in Orthopaedic Surgery"; 2007; Ed. Stiehl JB, Konermann WH, Haaker RG, Digioia AM, Springer Medizin Verlag, Heidelberg, pp. 378-384.
International Search Report and Written Opinion Based on PCT/IB2010/001807 Mailed Oct. 19, 2010.
Radermacher et al.; "Computer Assisted Orthopedic Surgery by Means of Individual Templates Aspects and Analysis of Potential Applications"; First International Symposiumon Medical Robotics and Computer Assisted Surgery; 1994; pp. 42-48.
PHD Thesis of Markus Fleute; "Non-Rigid 3D/3D Registration of Sparse Scattered Point Data With a Statistical Shape Model and Its Application to Computer Assisted ACL Surgery"; Universite Joseph Fourier; Grenoblem, France; 1999; Chapter 6.
Nogler; "Navigated Minimal Invasive Total Hip Arthroplasty"; Orthopaedic Surgery; Surg Tech. Int.; 2004; vol. 12; 2PP. 59-262.
Lewinnek et al.; "Dislocations After Total Hip-Replacement Arthroplasties"; J Bone and Joint Surg AM; Mar. 1978; vol. 60 A; No. 2; pp. 217-220; The Journal of Bone and Joint Surgery, Incorporated.
Sarin et al.; "Accurate Femur Repositioning is Critical During Intraoperative Total Hip Arthroplasty Leg Length and Offset Assesment"; J Arthroplasty; 2005; vol. 20; No. 7; pp. 887-891; Elsevier Inc.
Widmer et al.; "Compliant Positioning of Total Hip Components for Optimal Range of Motion"; J Orthop Res; 2004; vol. 22; pp. 815-821; Elsevier.
Duwelius et al.; "Minimally Invasive Total Hip Arthorplasty: An Overview of the Results"; AAOS Instructional Course Lectures; 2008; vol. 57; pp. 215-222.
D'Lima et al.; "The Effect of Oreintation of the Acetabular and Femoral Components on the Range of Motion of the Hip at Different Head-Neck Ratios"; The Journal of Bone and Joint Surgery-American; J Bone and Joint Surg; Mar. 2000; vol. 82 A; No. 3; pp. 315-321.
Wixson; "Computer-Assisted Total Hip Navigation"; AAOS Instructional Course Lectures; 2008; vol. 57; pp. 707-720.
Schmerwitz; "Total Hip Arthroplasty: First Experiences With Pinless THA Software to Determine Leg Length and Offset"; Orthopaedics; 2007; vol. 30; pp. S124-S126.
Della Valle et al.; "Preoperative Planning for Primary Total Hip Arthorplasty"; J American Academy of Orthopaedic Surgeons; 2005; vol. 13; No. 7; pp. 455-462; American Academy of Orthopaedic Surgeons.
Soong et al.; "Dislocation After Total Hip Arthroplasty"; J American Academy of Orthopaedic Surgeons; 2004; vol. 12; pp. 314-321.
Barrack; "Dislocation After Total Hip Arthroplasty : Implant Design and Orientation"; J American Academy of Orthopaedic Surgeons; Mar./Apr. 2003; vol. 11; No. 2; pp. 89-99; American Academy of Orthopaedic Surgeons.
Clark Rt al.; "Leg-Length Discrepancy After Total Hip Arthroplasty"; J American Academy of Orthopaedic Surgeons; 2006; vol. 14; pp. 38-45.; American Academy of Orthopaedic Surgeons.
Haaker et al.; "Comparison of Conventional Versus Computer-Navigated Acetabular Component Insertion"; The Journal of Arthroplasty; vol. 00 No. 0; 2005; pp. 1-8; Elsevier Inc.
Murphy; "Alumina Ceramic—Ceramic Total Hip Arthrplasty Using Computer—Assisted Surgical Navigation and a New Minimally Invasive Technique"; Advanced Ceramic Applications and New Projects; 9th Symposium 2.5; pp. 61-69.
Columbia St Mary's Stiehl News: Extract of Website Columbia St Mary's Milwaukee, Wisconsin—Columbia St Mary's Launches New Surgical Navigation for Orthopaedic Surgery.
Buckup et al.; "Minimally Invasive Implantation and Computer Navigation for a Unicondylar Knee System"; Mis; Extract From Ortho Supersite; Hawaii's Big Island Jan. 11-14, 2009.
Pregrant Publication Database Search Results.Pdf—List of Results of Search in PGPUB Production Database for : "Computer Assisted" and "Hip".
Stiehl et al.; "Principles of Computer Assisted Surgery"; Part V; Chapter 38; Technology; pp. 241-246.
Stiehl et al.; "Validation of Imageless Total Hip Navigation"; Part IV A; Chapter 42; Navigation: Total Hip Arthroplasty; pp. 334-338.
Stiehl et al.; "Accuracy of Acetabular Component Positioning With a Fluoroscopically Referenced CAOS System"; Computer Aided Surgery; Sep./Nov. 2005; 10(5/6); pp. 321-327; Taylor & Francis.
Stiehl et al.; "Validation and Metrology in CAOS"; Extracted on Dec. 9, 2006; Chapter 9; pp. 68-78.
Radermacher et al.; "Computer Integrated Advanced Orthopedics (CIAO)"; ESME; Stuttgart, Germany; 1993.
Radermacher er al.; "Computer Assisted Matching of Planning and Execution in Orthopedic Surgery"; 1993; IEEE EMBS; San Diego; U.S.A.
Eckhoff et al.; "Three-Dimensional Mechanics, Kinematics, and Morphology of the Knee Viewed in Virtual Reality"; JBJS; 2005; vol. 87; pp. 71-80; The Journal of Bone and Joint Surgery.
Coughlin et al.; "Tibial Axis and Patellar Position Relative to the Femoral Epicondylar Axis During Squatting"; Journal of Arthroplasty; Dec. 2003; vol. 18; No. 8; pp. 1048-1055.

\* cited by examiner

ADJUSTABLE GUIDE IN COMPUTER ASSISTED ORTHOPAEDIC SURGERY

CROSS REFERENCE TO RELATED APPLICATIONS

This application is a §371 National Stage Application of PCT/EP2010/001938, filed Jun. 29, 2010, which claims priority to U.S. Provisional Application No. 61/221,639, filed Jun. 30, 2009.

BACKGROUND OF THE INVENTION

1. Field of the Invention

The present invention relates to a method and device that accelerates the placement of cutting guides in orthopaedic surgery, such as for instance total knee arthroplasty, uni knee arthroplasty or knee revision procedures, by taking the advantage of pre-operative patient images and intra-operative navigation systems and avoiding the drawbacks of patient specific guides manufactured as solid blocks, which do not offer enough flexibility, and avoiding drawbacks of navigation systems, which usually require additional steps in the surgical workflow.

2. Description of Related Art

It is known that patient specific guides are generated from preoperative CT (Computed Tomography) or MR (Magnetic Resonance) images, such that after surgical planning based on patient images, rapid machining of a specific guide is performed. The resulting guide is a solid block which is positioned in a supposedly unique and reproducible manner on the patient bone or cartilage surface, using surface contact areas, such that the guide contains holes or cutting slots adjusted precisely to their planned position on patient images. For instance, Radermacher K, and Staudte H. W. disclose in "Computer Assisted Orthopedic Surgery by means of Individual Templates", Rau G. 1994, Medical Robotics and Computer Assisted Surgery, pp 42-48, a specific guide machined from CT images. Such patient specific guides require specific machining and a complex process where many errors can occur, which adds time and cost to the procedure. This is a major drawback. Such templates are usually disposable and machined for each patient which generates time and logistics issues before surgery. In addition, a difference between the bone or cartilage surface that is accessed intra-operatively and the surface of the bone or cartilage which is modeled from patient images may differ by one or several millimeters at some points. This can occur for instance because of the presence of osteophytes that are not easily visible on images, or because of the presence of small debris of soft tissues. They can create deviations of the orientation of the guides by several degrees from their planned position. In addition, the surgeon might have to change the planned position of an implant during the surgery to take into account the specificity of elements not visible or measurable on patient images, such as for instance the ligament behavior between the femur and the tibia in knee arthroplasty. And finally the patient specific guides for knee prosthesis require taking images, in addition to the knee joint, of the hip and ankle areas which are not standard radiology protocols for knee examination.

It is known to design adjustable templates from CT images for spine surgery with a small and minimal number of adjustments so that those adjustments can be performed by adjusting positions manually.

It is known that some navigation systems are tracking instrument positions during their adjustment, with respect to patient specific points, surfaces or articulations, and that some cutting blocks are tracked in real-time by navigation of bone cuts in particular for knee replacement procedures. It is known that some cutting blocks have mechanisms such that the cutting plane position can be adjusted with a few screws to reach precisely a target position defined on the basis of anatomical landmarks. Existing navigation systems require additional fixations to attach a tracker on the tibia and a tracker on the femur. This is a major drawback of navigation systems. Surgeons and patients are more and more reluctant to make additional holes into the bone for navigation purpose, because it creates additional scars, it increases the fragility of the bone and it adds time to the procedure. In addition, image free navigation systems do not offer the possibility to make a predetermination of the size of the implant preoperatively. In addition, some surgeons have difficulties to adjust the cutting blocks to predefined values, which require additional time and efforts.

The goal of the invention is to propose a device and method that solve the drawbacks of both patient-specific guides and navigation systems in order to offer a safe, easy-to-use and fast solution for positioning cutting guides on the basis of preoperative CT or MR images whilst maintaining enough flexibility to incorporate adjustments intra-operatively.

SUMMARY

A first object of the invention is a surgical device, for the purpose of adjusting cutting blocks to a desired position with respect to a bone of a patient, comprising:
- an adjustable guide with at least six and preferably more than twelve adjustable screws whose length is calculated to create a contact point when the adjustable guide is in its desired position planned on preoperative CT or MR images,
- wherein the adjustable guide comprises two pairs of holes that guide pins which position and fix said cutting blocks,
- a dedicated screwdriver to adjust the position of each screw to its target value,
- a navigation system which is used to check the correct position of the adjustable guide with respect to anatomical points.

Another object of the invention is a surgical device, for the purpose of adjusting cutting blocks to a desired position with respect to a bone of a patient, the device comprising:
- an adjustable guide with at least six and preferably more than twelve adjustable screws whose length is calculated to create a contact point when the adjustable guide is in its desired position planned on preoperative CT or MR images,
- wherein the adjustable guide comprises one cutting block and one pair of holes that guide pins which position and fix a cutting block,
- a dedicated screwdriver to adjust the position of each screw to its target value,
- a navigation system which is used to check the correct position of the adjustable guide with respect to anatomical points.

According to an embodiment of the invention, the adjustable guide is articulated to two cutting blocks or pairs of holes with three adjustable screws.

According to an embodiment of the invention, the adjustable guide is articulated to one cutting block or pair of holes with three adjustable screws and the cutting block or pair of holes is articulated with a pair of holes with two adjustable screws.

Preferably, the dedicated screwdriver is motorized and controlled by a computer in order to adjust the length of each screw automatically to their target position.

Another object of the invention concerns a method of adjusting cutting blocks to a desired position with respect to a bone of a patient that comprises the following steps:
 (1) Acquisition of CT or MR images and planning of an implant position
 (2) Extraction of the bone and cartilage surfaces from said images
 (3) Calculation of the screw lengths contained in an adjustable guide for said cutting blocks such that the adjustable guide is in its desired position when the screws are in contact with the bone and cartilage surface
 (4) Adjustment before the surgery of the screws of the adjustable guide to their target position using a dedicated screwdriver
 (5) Position the adjustable guide in contact with the surface and check using a navigation system that the adjustable guide is in a correct position with respect to anatomical points or with respect to additional patient data collected intra-operatively
 (6) Iterate steps (3) or (4) until the condition of step (5) is met.

Another object of the invention is a surgical device, for the purpose of adjusting cutting blocks to a desired position with respect to a bone of a patient, the device comprising:
 an adjustable guide made of several parts connected together by adjustment mechanisms with screws
 a navigation system which is used to check the correct position of the parts of the adjustable guide with respect to anatomical data.

Said anatomical data are advantageously CT or MR images of the patient registered with the adjustable block position.

The method of the invention is using five steps.

The first step of the method consists in acquiring patient images that can be CT or MR images and then performing a surgical planning of an implant position on those images using a computer with display and man machine interactions. The planning defines the position of the prosthesis and therefore the position of the cutting planes necessary to insert the prosthesis. Cutting planes can be associated with pairs of pins on which cutting block can slide and be fixed.

In the second step, it is necessary to extract the bone or cartilage surface on patient CT or MR images.

In the third step, the virtual position of an adjustable guide position is defined on the patient images. Without any limitation of the invention, the description relates to a femoral guide for total knee arthroplasty. In a preferred embodiment, the adjustable guide contains two holes rigidly connected that will drive pins to be used in order to position and hold a distal cutting guide, and two holes rigidly connected that will drive pins to be used in order to position and hold a cutting block that contains usually four slots that guide a saw blade for performing four cuts in the bone, known as four-in-one cutting block, such that those four cuts and the distal cut make together five cuts that match precisely the internal shape of the prosthesis. The first pair of holes can be also replaced by a cutting slot that guides the saw blade directly for performing the distal cut. The position of the two pairs of holes is easily calculated such that the cutting guide and cutting blocks will match the internal shape of the implant of which the external shape has been adjusted during the planning step. From that calculation, the position of the adjustable guide that contains the two pairs of holes is known with respect to the patient images, and therefore with respect to the bone or cartilage surface detected in step 2. The adjustable guide contains series of many screws, at least 6, preferably more than 12. The screws do not need to have parallel axis, but have known direction and zero offset positions in relation to the pairs of holes. The tip of the screws can have different shapes. Preferably the tip of the screws is a hemisphere with a radius ranging from 1 to 12 mm, or more generally a portion of a sphere. The tips of the screws must come in contact with the bone surface or cartilage detected in step 2. An algorithm is used to compute the length of each individual screw such that its spherical tip will come in perfect contact with the surface of the bone or cartilage. This algorithm consists in virtually sliding the sphere along the axis of the screw every tenth of millimeter and for each point of the axis computing the closest distance to the surface using known point-to-surface distance calculation methods. When the distance reaches the radius of the sphere of the screw tip, the contact is detected and the screw length is memorized. At the end of that step, one collects for a specific adjustable guide a list of pairs indicating a screw number and a screw length, with a global score that must be above a fixed threshold. Preferably, this list of pairs is stored on an output computer file through any media such as USB key, CD-ROM or internet transfer file.

In the fourth step, the adjustable guide is prepared for surgery from the output file obtained at the previous step. This preparation can be performed by an assistant before the first incision of the patient. It is possible to adjust the screws manually using a graduation on each screw. But this process is time consuming and prone to error. Preferably, a dedicated screw driver is used. In a preferred embodiment, the screw length is easy to read and adjust. For that purpose, the dedicated screw driver contains an external tube that comes into contact with the exterior part of the adjustable guide by using a spring that pushes the tube towards the guide and it contains a tip that can fit with the head screws at a unique depth such that when the screwdriver tip is engaged on the screw head, the length of the screw is uniquely determined with respect to the external surface of the guide. Therefore, the relative displacement between the external tube and the screwdriver tip is the screw length with a known offset that can be subtracted. This relative displacement can be measured and read electronically like for any standard digital calipers square. It can be output to a computer with a display monitor. The user reads the value for each screw number and adjusts the screw length manually until it matches precisely the desired target. In a second preferred embodiment, the dedicated screwdriver is motorized and communicates with a computer through a wire connection including power supply, or preferably through wireless communication with batteries. The readings from the electronic length sensor are sent to the computer. For a given screw, the motors are activated in one or other direction until the readings match the desired value. Some standard optimized control can be implemented to speed the convergence of each screw towards its target position. In addition, the screw number can be detected automatically by using a variety of recognition techniques implemented in the screw heads, such as optical, inductance, magnetic detection technologies. This embodiment has the advantage that the program of the computer can check that all screws have been adjusted and none is missing. When all screws have reached their target position, the adjustable guide can be positioned by the surgeon on the patient and the surgeon can estimate if the fit is good or not, using tactile sensing. The adjustable guide is sterile. It is preferably a metallic instrument that can be sterilized in autoclave or a disposable plastic instrument pre sterilized for single use.

In the fifth step, a navigation system is used to check that the guide is in a correct location. For instance, for a femoral guide, once the adjustable guide is locked in a unique position on the femur, a tracker is attached to it and the surgeon performs a standard hip pivot kinematics from which any standard image free navigation system can extract the hip center. The relationship between the tracker and the adjustable guide is known precisely. The determination of the hip center in the coordinate system of the adjustable guide is used to check that the distal cut will be orthogonal to the axis passing through the knee center determined as a point, fixed or variable, in the coordinate system of the adjustable guide and the hip center, or that a predefined angle selected by the surgeon has been reached. This step is extremely important since a small deviation in the contact points of the adjustable guide can lead to several degrees of error on that angle, which is known to impact the longevity of the implant. This process is repeated until the values match the desired angle. In addition, the surgeon can decide to adjust the planning position intra-operatively to take into account new information such as ligament balancing and desired gaps between the femur and the tibia at several flexion angles of the leg, obtained for instance with the help of a tensor mechanism. It can be also decided during surgery to change the size of the prosthesis. The computer will indicate precisely which screws will need to be adjusted since the computer program can estimate the location of the surface of bone and cartilage from the registered position of the adjustable guide. The computer can also indicate if a bigger or smaller size of the adjustable guide is necessary to reach the desired target. Once the guide is in its final position, the surgeon inserts pins in the holes and the guide is removed. Cutting blocks are inserted on the pins and the surgery can proceed as usual. Several mechanical architectures and designs can be implemented to introduce more flexibility in the adjustment mechanism as it will be described in the detailed description.

All steps can be performed in parallel for managing several implants, for instance femoral, tibial and patella implants for knee surgery.

DETAILED DESCRIPTION OF A PREFERRED EMBODIMENT

The tracking technology of trackers and navigation systems is independent of the invention, provided that the trackers are tracked in real-time by the navigation system. It includes, but is not limited to optical active technology, with active infrared Light Emitting Diodes (LEDs) on trackers, optical passive technology (with passive retro-reflective markers on trackers), mechanical passive arms with encoders, radio-frequency measurements, gyro meters and accelerometers or magnetic technology. Those tracking technologies are known as prior art of navigation systems for surgery.

Figure 1:
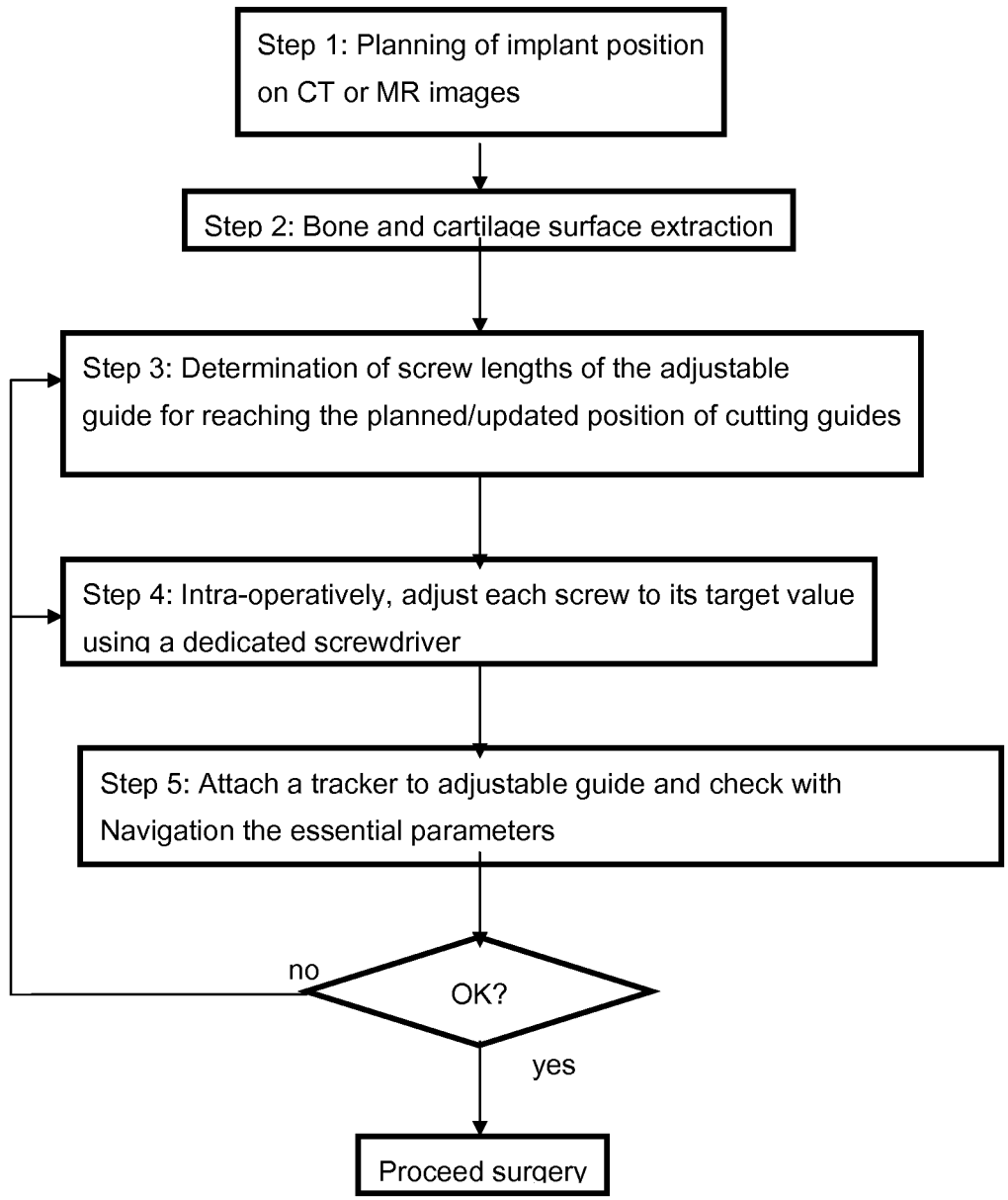
FIG. 1 is a summary of the method of the invention that presents a surgical procedure flow diagram with the five steps and the possibility to iterate the last steps.

FIG. 1 presents the successive steps of the method according to the invention.

The first step of the method consists in acquiring patient images that can be CT or MR images and then performing a surgical planning of an implant position on those images using a computer with display and man machine interactions. The patient images can also be provided by intra-operative three-dimensional fluoroscopy devices which acquire many x-ray projections and reconstruct from those projections a three-dimensional image during surgery; it represents a particular case of Computed Tomography (CT). The planning can be performed by detecting specific landmarks on the patient images with the mouse and adjusting the position of implants to the landmarks according to known criteria, and adding the possibility for the surgeon to adjust the position interactively with visual control using three-dimensional visualization. This step is used in several existing products: Materialize (Leuven, Belgium), Otismed (Alameda, Calif., USA). In the standard approach, the planning uses hip and ankle centers detected on images, which is a possible option of the method of the invention. In a preferred embodiment, the planning for knee prosthesis is performed using the knee joint images only, without needs to define the hip and ankle centers precisely. A standard estimate of the direction of the femoral axis of the femur is for instance 7 degrees internal with respect to the anatomical axis which is easy to detect on knee joint images. The tibial mechanical axis can be confounded with the anatomical axis which is easy to define on knee joint images. Those represent only approximations that will be checked and refined during the navigation step. In the proposed method, it is the surgeon choice to include the hip and ankle centers in the images which also depends on the patient, the possibility to make special radiology protocols or not, and the cost of such extra examination versus standard examination.

In the second step, it is necessary to extract the bone or cartilage surface 5 on patient CT or MR images. MR images provide a better definition of cartilage but the fully automated detection of the global external surface of the cartilage on those images is a difficult process. Usually, manual delineation of contours of the cartilage by experts is used to obtain such surface. Preferably, an automated detection of the cartilage local and partial external surface is obtained by searching for contours in a predefined small area. Indeed, from the planning of a prosthesis defined in the first step, one knows the approximate location of the cartilage surface as the external surface of the implant. Such surface can then be deformed and shrunk locally to adjust the contours using morphing methods described in the PhD thesis of Markus Fleute (University Joseph Fourier, Grenoble, France, 1999). Checking that such algorithms have converged properly is achieved only in local areas that will be necessary in the third step, which can be done visually or automatically by checking the quality of surface detection in those areas, which is for instance proportional to image gradient intensity. The same principle can be used to detect bone and cartilage on CT images. The choice between cartilage and bone depends on the contact surfaces which are chosen, it is also possible to have a combination of surface contacts on cartilage and surface contacts on bone. It is also possible to merge CT and MR images to constitute a complete, accurate and reliable representation of the surfaces.

Figure 2:
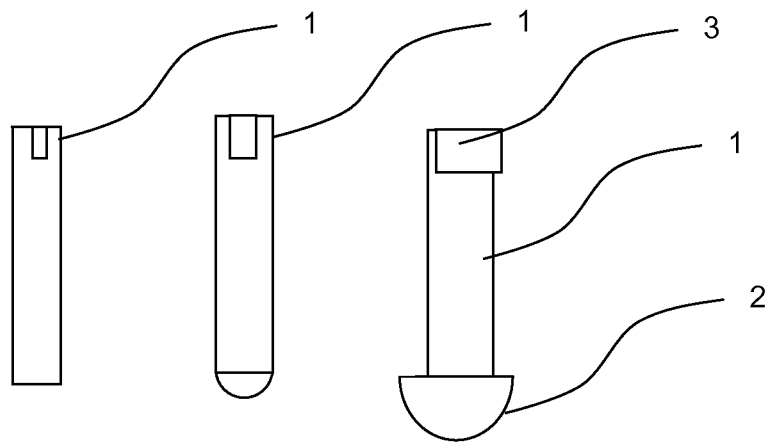
FIG. 2 is a view of the different types of screws that can be used for adjusting the guide.
Figure 3:
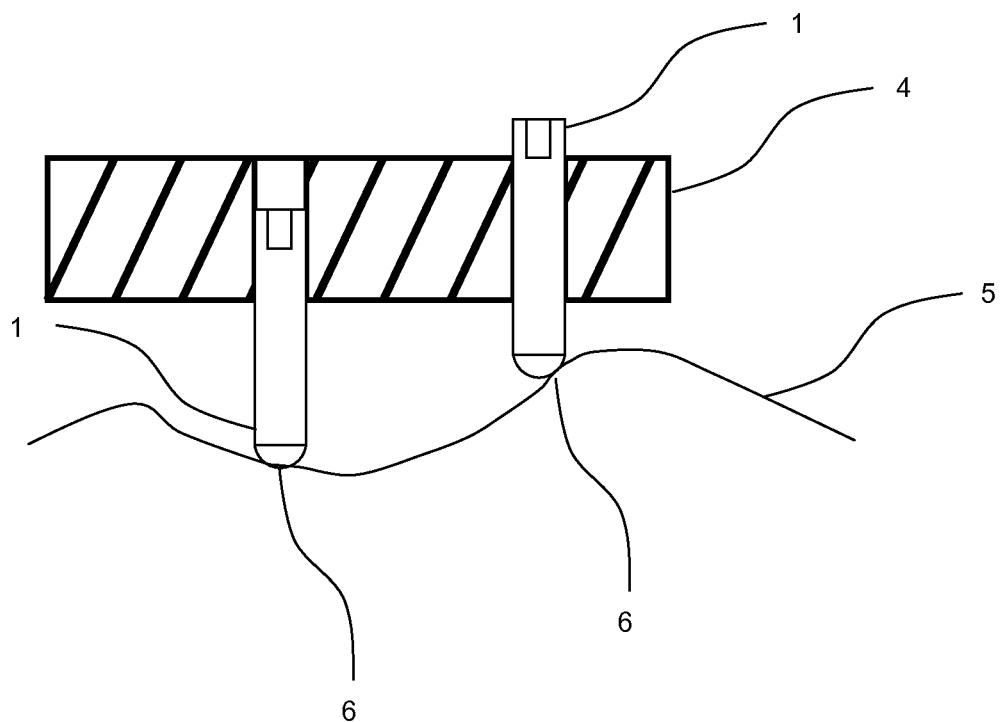
FIG. 3 is a cut of a part of the adjustable guide with two screws that enter in contact with the bone surface
Figure 5:
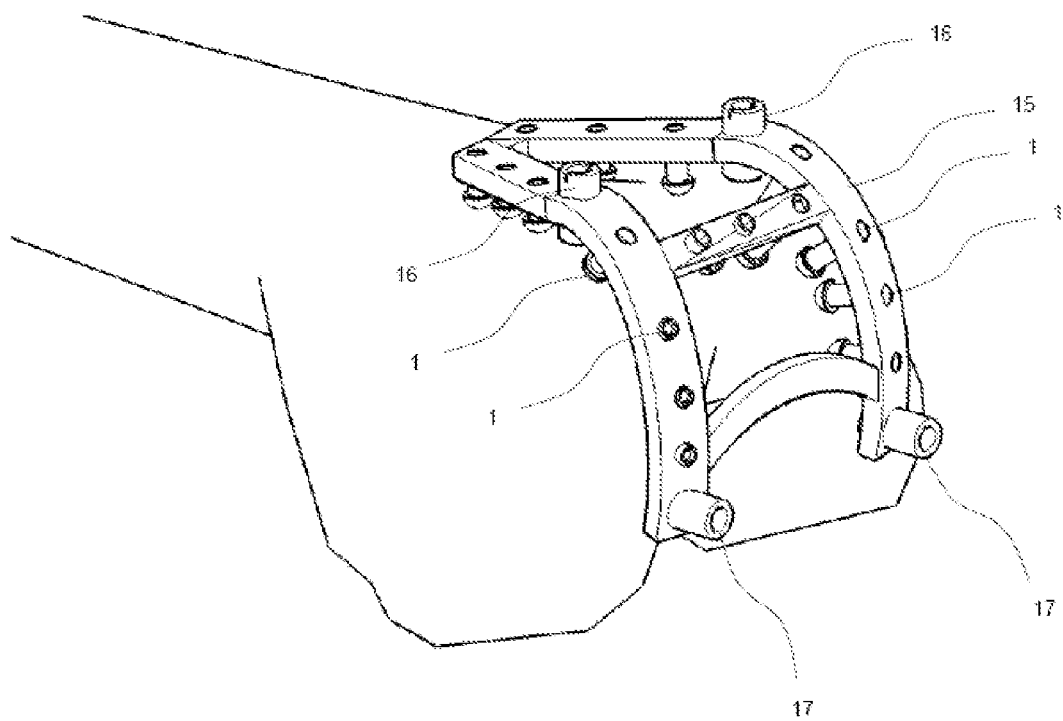
FIG. 5 is an oblique view of the adjustable guide with two pairs of holes and 17 additional screws.

In the third step, the virtual position of an adjustable guide position is defined on the patient images. Without any limitation of the scope of the invention, the description relates to a femoral guide for total knee arthroplasty. In a preferred embodiment, shown on FIG. 5, the adjustable guide 15 contains two holes rigidly connected 16 that will drive pins to be used in order to position and hold a distal cutting guide, and two holes rigidly connected 17 that will drive pins to be used in order to position and hold a cutting block that contains usually four slots that guide a saw blade for performing four cuts in the bone, known as four-in-one cutting block, such that those four cuts and the distal cut make together five cuts that match precisely the internal shape of the prosthesis. Using two parallel pins to guide and fix a cutting block that slides on the pins until it comes in contact with the bone is a standard approach used in most of knee surgeries. It is also possible to add more cutting slots and more holes to the guide. As shown on FIG. 7, the first pair of holes can be also replaced by a cutting block 18 that guides the saw blade directly for performing the distal cut inside a slot 19. The position of the two pairs of holes is easily calculated such that the cutting guide and cutting blocks will match the internal shape of the implant of which the external shape has been adjusted during the planning step. The two pairs of holes 16 and 17 are supposed to be orthogonal, but the invention can be easily extended if it is not the case. From that calculation, the position of the adjustable guide 15 that contains the two pairs of holes is known with respect to the patient images, and therefore with respect to the bone or cartilage surface 5 detected in step 2. The adjustable guide contains series of many screws 1, at least 6, preferably more than 12. The screws do not need to have parallel axis, but have known direction and zero offset positions in relation to the pairs of holes. The head screw 3 is preferably inside the shaft of the screw in order to minimize the external envelope of the adjustable guide and maintain it smooth. The tip 2 of the screws can have different shapes for which examples are represented in FIG. 2. Preferably the tip 2 of the screws is a hemisphere with a radius ranging from 1 to 12 mm, or more generally a portion of a sphere. The tips of the screws must come in contact with the bone surface or cartilage detected in step 2. An algorithm is used to compute the length of each individual screw 1 such that its spherical tip will come in perfect contact with the surface of the bone or cartilage. This algorithm consists in virtually sliding the sphere along the axis of the screw every tenth of millimeter and for each point of the axis computing the closest distance to the surface using known point-to-surface distance calculation methods. When the distance reaches the radius of the sphere of the screw tip, the contact point 6 is detected and the screw length is memorized. Such algorithm can be easily optimized by search techniques along the screw axis. The diameter of the spheres can be different for each screw. This process is detailed in FIG. 3 in which a cut 4 of the adjustable guide 15 is represented. For a given position of the guide 4 and 15 with respect to the surface 5, a unique length of the screws Li (wherein i is an integer comprised between 1 and the total number of screws) can be computed to obtain a contact point 6. Each value of Li can be positive if the screw head is below the external surface of the adjustable guide 4 and 15, or negative if the screw head is above the external surface. In the design of the mechanical guide, it is recommended to avoid negative distances of the screws Li since they can damage soft tissues of the patient. But on the other hand, high positive values will be obtained with a thick or large adjustable guide, which is not acceptable for minimally invasive surgery. Therefore, several designs can be proposed with different sizes and shapes, for instance a small, a medium and a large design. The method globally checks that each screw is in the range of possible lengths for the given local thickness and position of the adjustable guide 4, and if not it suggests another adjustable guide size or shape, or it proposes to use extra length or extra short screws, or it removes said inaccessible screws. The method can check that the contact points 6 are in sufficient number and with sufficient distribution such that the fitting with the surface will be unique and stable, this can be achieved by scoring the uncertainty of the fit between this cloud of points 6 and the surface 5; the problem can be formulated as a least squares fitting in which the norm of the hessian matrix represents an approximation U of the uncertainty. At the end of that step, one collects for a specific adjustable guide a list of pairs indicating a screw number i and a screw length Li, with i varying from 1 to N, where N is the total number of screws, with a global score U that must be above a fixed threshold. Preferably, this list of pairs (i, Li) stored on an output computer file through any media such as USB key, CD-ROM or internet transfer file. On the same file, the planned position of the implant and the images are stored. If all screws have their length adjusted to the determined value, and if the adjustable instrument is placed in contact to the bone and cartilage by the surgeon, its position is unique and corresponds to the position for which the pairs of holes match the planned position of cutting guides.

Figure 4:
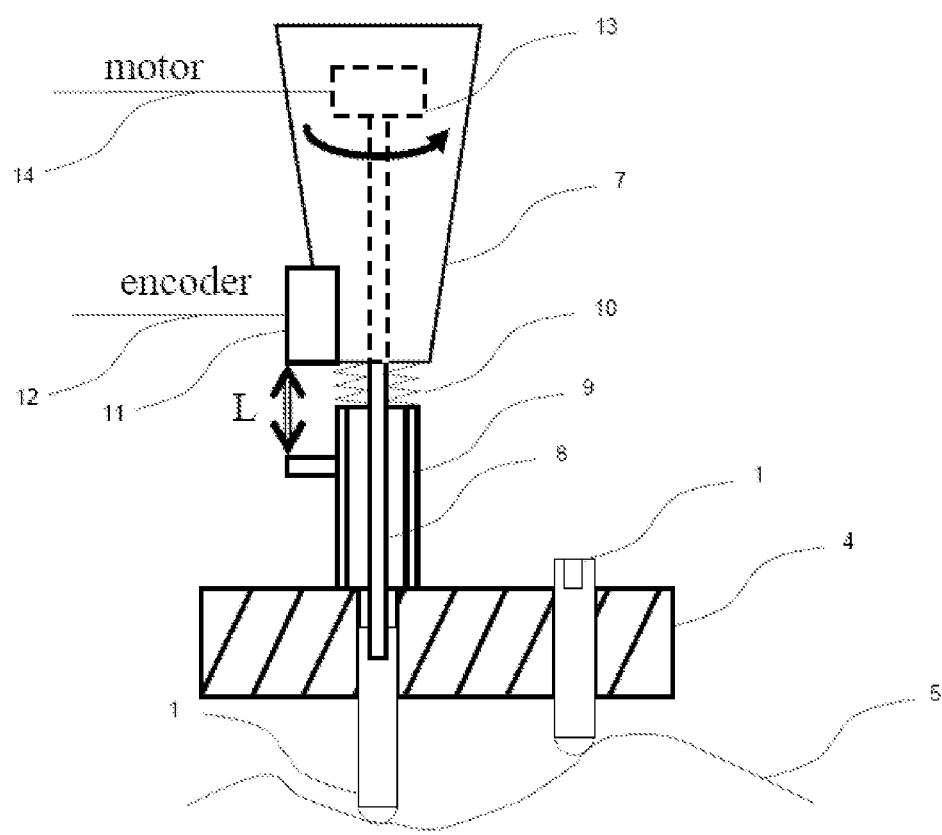
FIG. 4 is the same cut as in FIG. 3 with a drawing of the dedicated screwdriver with sensing and motorized mechanisms.

In the fourth step, the adjustable guide is prepared for surgery from the output file obtained at the previous step. This preparation can be performed by an assistant before the first incision of the patient. It is possible to adjust the screws manually using a graduation on each screw. But this process is time consuming and prone to error. Preferably, a dedicated screw driver 7, as shown on FIG. 4, is used. In a preferred embodiment, the screw length is easy to read and adjust. For that purpose, the dedicated screw driver contains an external tube 9 that comes into contact with the exterior part of the adjustable guide 4 by using a spring 10 that pushes the tube towards the guide and it contains a tip 8 that can fit with the head screws at a unique depth such that when the screwdriver tip is engaged on the screw head, the length of the screw is uniquely determined with respect to the external surface of the guide. Therefore, the relative displacement L between the external tube and the screwdriver tip is the screw length with a known offset that can be subtracted. This relative displacement can be measured and read electronically like for any standard digital calipers square using a linear encoder 11. It can be output to a computer through a cable 12 to a standard display monitor that can be the same as the navigation system, or by using wireless communication and embedded batteries. The user reads the value for each screw number and adjusts the screw length manually until it matches precisely the desired target that is displayed nearby. It is also possible to display the difference between the actual length and the desired length and the target becomes to assign zero on every screw. In a second preferred embodiment, the dedicated screwdriver is motorized with an internal low energy motor 13 that communicates with a computer through a wire connection 14 and external power, or preferably through wireless communication with batteries. The readings from the electronic length sensor are sent to the computer. For a given screw, the motor 13 is activated in one or other direction until the readings match the desired value. Some standard optimized control can be implemented to speed the convergence of each screw towards its target position. In addition, the screw number can be detected automatically by using a variety of recognition techniques implemented in the screw heads 3, such as optical, inductance, magnetic detection technologies. This embodiment has the advantage that the program of the computer can check that all screws have been adjusted and none is missing. When all screws have reached their target position, the adjustable guide 15 can be positioned by the surgeon on the patient surface 5 and the surgeon can estimate if the fit is good or not, using tactile sensing. The adjustable guide is sterile. It is preferably a metallic instrument that can be sterilized in autoclave or a disposable plastic instrument pre sterilized for single use.

Figure 6:
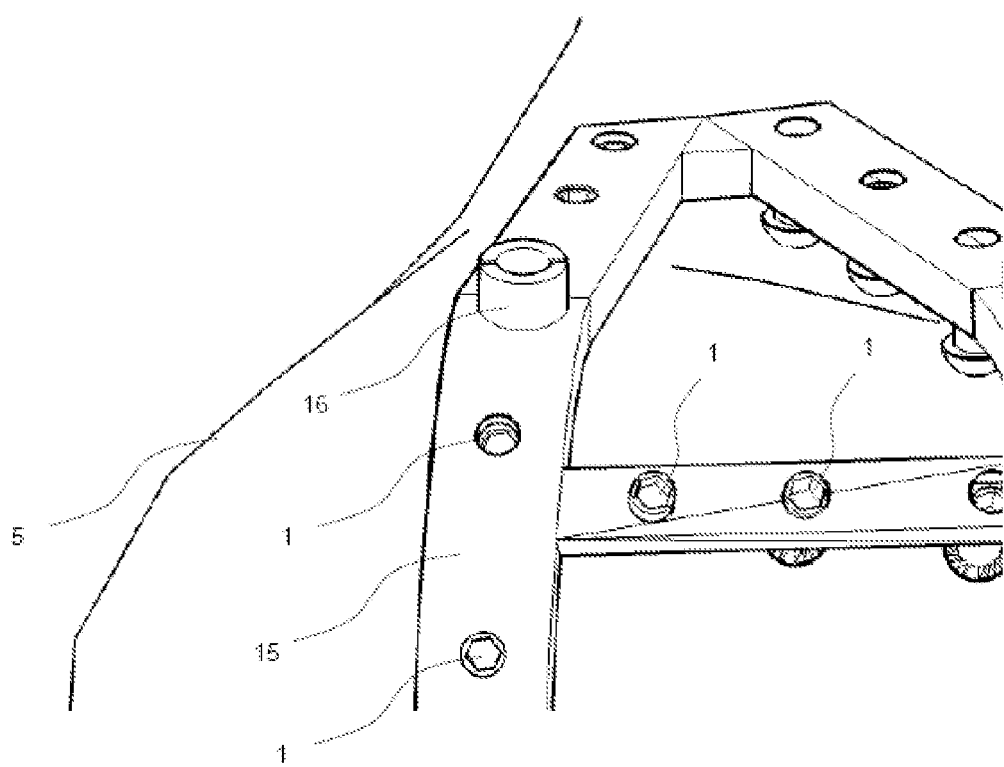
FIG. 6 is a detailed view of a portion of the adjustable guide

In the fifth step, a navigation system is used to check that the guide is in a correct location with respect to anatomical points acquired intra-operatively. For instance, for a femoral guide, once the adjustable guide is positioned manually on the bone and locked by the contact points of the screw tips in a unique position on the femur, a tracker (not represented) is attached to it with a reproducible clip fixation and the surgeon performs a standard hip pivot kinematics from which any standard image free navigation system can extract the hip center as a reference anatomical point. The relationship between the tracker and the adjustable guide is known precisely. The determination of the hip center in the coordinate system of the adjustable guide is used to check that the distal cut will be orthogonal to the axis passing through the knee center determined as a point, fixed or variable, in the coordinate system of the adjustable guide and the hip center, or that a predefined angle selected by the surgeon has been reached. This step is extremely important since a small deviation in the contact points 6 of the adjustable guide can lead to several degrees of error on that angle, which is known to impact the longevity of the implant. It is an essential parameter that needs to be checked. The surgeon can decide if other essential parameters need to be checked with respect to additional points obtained by the navigation system, such as distance to the most distal condyle, or rotation with respect to posterior condyles. On the tibia, a similar process is used to digitize the ankle center by the palpation of the malleoli with a navigation pointer. If the angle measured with the navigation system is not the correct expected angle, the computer of the navigation system can indicate which screws are necessary to adjust in order to reach the desired angle. This process is repeated until the values match the desired angle. If the iterative process is estimated too long or too time consuming, the surgeon can decide to switch to standard image-free navigation without using the patient pre-operative data, preferably with the same adjustable guide or with any other navigated instruments. In addition, the surgeon can decide to adjust the planning position intra-operatively to take into account new information such as ligament balancing and desired gaps between the femur and the tibia at several flexion angles of the leg, obtained for instance with the help of a tensor mechanism. It can be also decided during surgery to change the size of the prosthesis. The computer will indicate precisely which screws will need to be adjusted since the computer program can estimate the location of the surface of bone and cartilage from the registered position of the adjustable guide. The computer can also indicate whether a bigger or smaller size of the adjustable guide is necessary to reach the desired target. Once the guide is in its final position, the surgeon inserts pins in the holes and the guide is removed. Cutting blocks are inserted on the pins and the surgery can proceed as usual. FIG. 6 shows a detailed view of the adjustable guide 15. Preferably, the holes 16 and 17 can also be adjustable and have a spherical tip that enters in contact with the surface, thereby easily adding four contact points. For that purpose, the dedicated screwdriver must have a dedicated tip or bridge that fits with the plot 16 in order to screw it or unscrew with respect to the guide 15.

Figure 7:
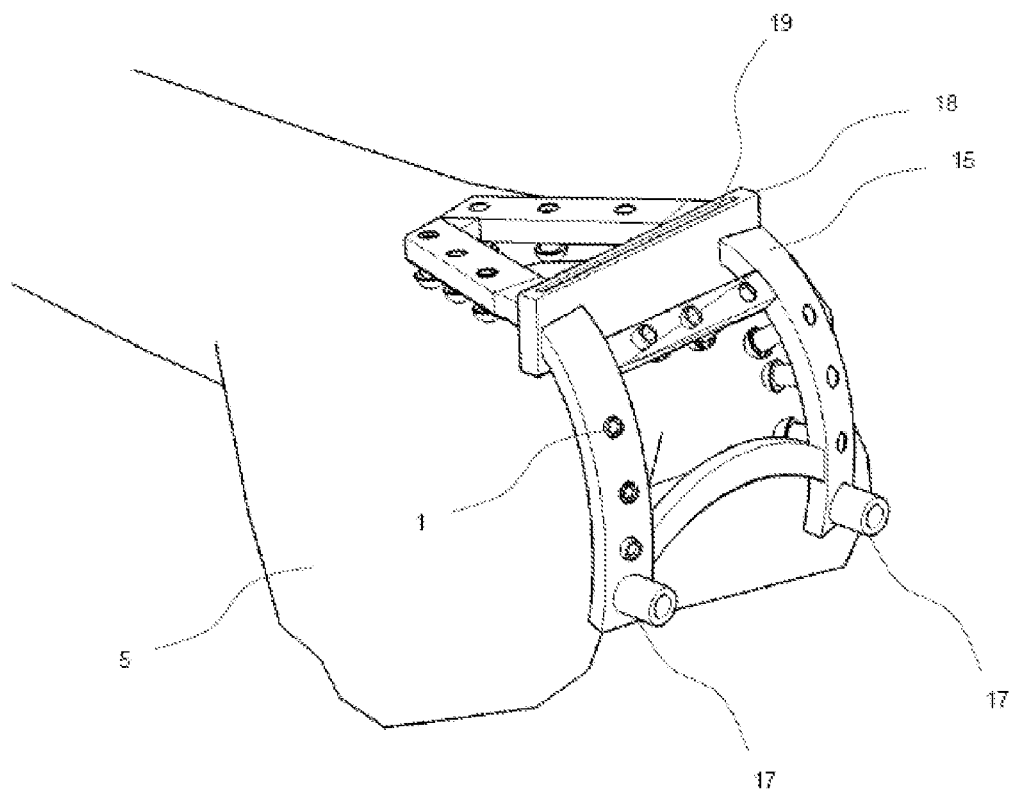
FIG. 7 is an oblique view of the adjustable guide with one pair of hole and one cutting slot.

In another preferred embodiment of the invention represented on FIG. 7, the pair of holes 16 can be replaced by a cutting block 18 with a slot 19 for guiding directly the saw blade as any conventional distal guide.

Figure 8:
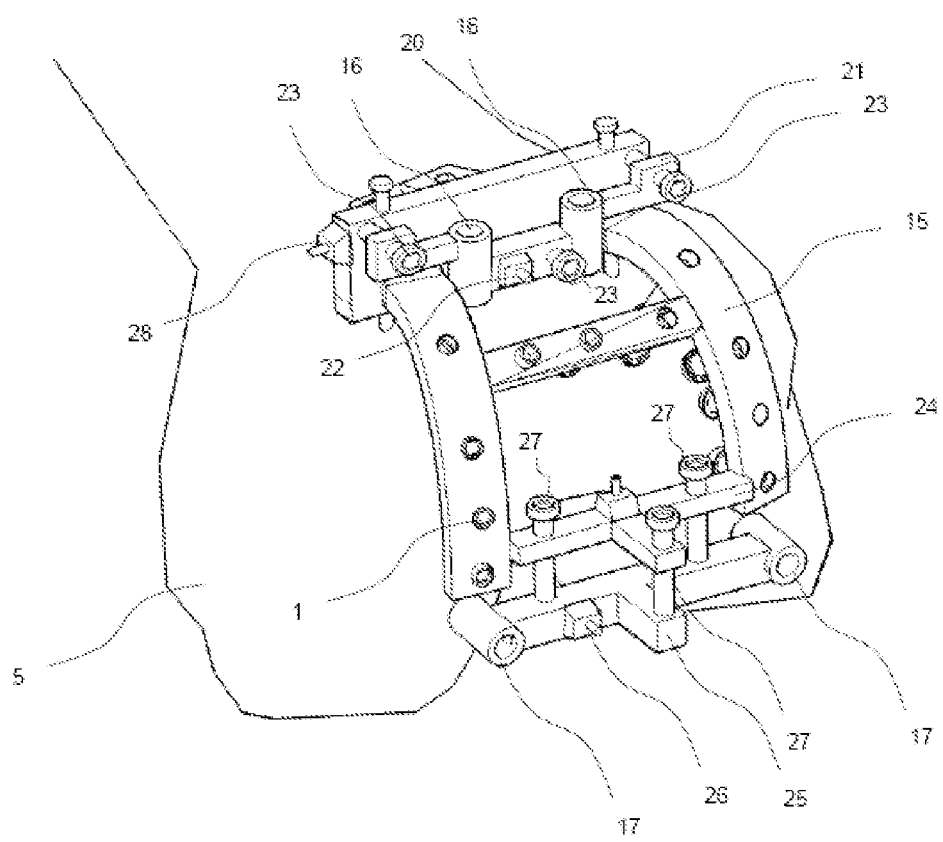
FIG. 8 is an oblique view of the adjustable guide with a fixed part and two independent adjustable parts.

In another preferred embodiment of the fourth and fifth steps, the adjustable guide is made of at least two parts A and B connected together by adjustment mechanisms with three additional screws. The part A follows the same principle as described previously and contains a plurality of small screws that enter in contact with the bone or cartilage surface. The screws lengths of part A are adjusted according to the computation of contact points between the surface and the screw axis as described previously. Part A can be fixed to the bone with pins if the surgeon estimates that the manual fit between surfaces is not strong enough. Part B contains a cutting guide or two holes that will guide pins on which a cutting guide can be mounted. The three screws that link A and B are adjusted with the dedicated screwdriver such that part B will match the position of the cutting plane defined during the planning phase. Part B may also contain screws that generate a contact point with the bone or cartilage. It is also possible to add a part C that links to part A for adjusting a second guide with holes or slots, such as for instance the holes for pins of the four-in-one cutting blocks of knee prosthesis, using three screws to adjust the relation between parts A and C. The use of three screws between parts A and B, and between parts A and C, is related to the fact that a plane adjustment needs exactly three degrees of freedom. Several mechanisms with three screws can be used, preferably a stiff mechanism in which the screws are roughly parallel. The advantage of this solution is that adjustments decided by the surgeon because of errors in the positioning detected with the navigation system or adjustments decided by the surgeon intra-operatively for taking into account new patient data can be made easily on the few screws that link part A to part B and part A to part C without touching the numerous screws that create and maintain the fit with the bone or cartilage surface. FIG. 8 details the described mechanism. The part 20 is rigidly connected to the basis of the adjustable guide 15 that contains the adjustable screws 1. An adjustable part 21 is connected to part 20 by three screws 23 and it contains the holes of the distal cut 16 (or equivalently a cutting block) and it contains also a reproducible attachment for a navigation tracker 22. The basis 15 remains stable on the knee surface and only the adjustment of the screws 23 is performed to match an updated position of the plane defined by the holes 16. During the adjustment of these three screws, the tracker attached to the second basis 24 through 26 is used as a fixed reference, or a second tracker fixation 28 can be used. When the holes 16 have reached their desired position, two pins are inserted through the holes. Similarly, the part 24 is rigidly connected to the basis 15. A second adjustable part 25 is connected to 24 by three screws 27 and it contains the holes 17 of the 4-in-1 cutting block and it also contains a reproducible attachment to a navigation tracker 26. The basis 15 remains stable on the knee surface and only the adjustment of the screws 27 is performed to match an updated position of the plane defined by the holes 17. During the adjustment of these three screws, the tracker attached to the first basis through 22 is used as a fixed reference, or a second tracker fixation 28 can be used. When the holes 17 have reached their desired position, two pins are inserted through the holes. To disassemble the system, the last two pins are removed, the unnecessary guides are removed and the distal cut is performed. Then, the holes made in the bone are found by the surgeon who inserts two new pins and the four-in-one cutting block is inserted and fixed. The cuts are preformed in a conventional way. In such design, part A is 15, part B is 21 and part C is 25.

Figure 9:
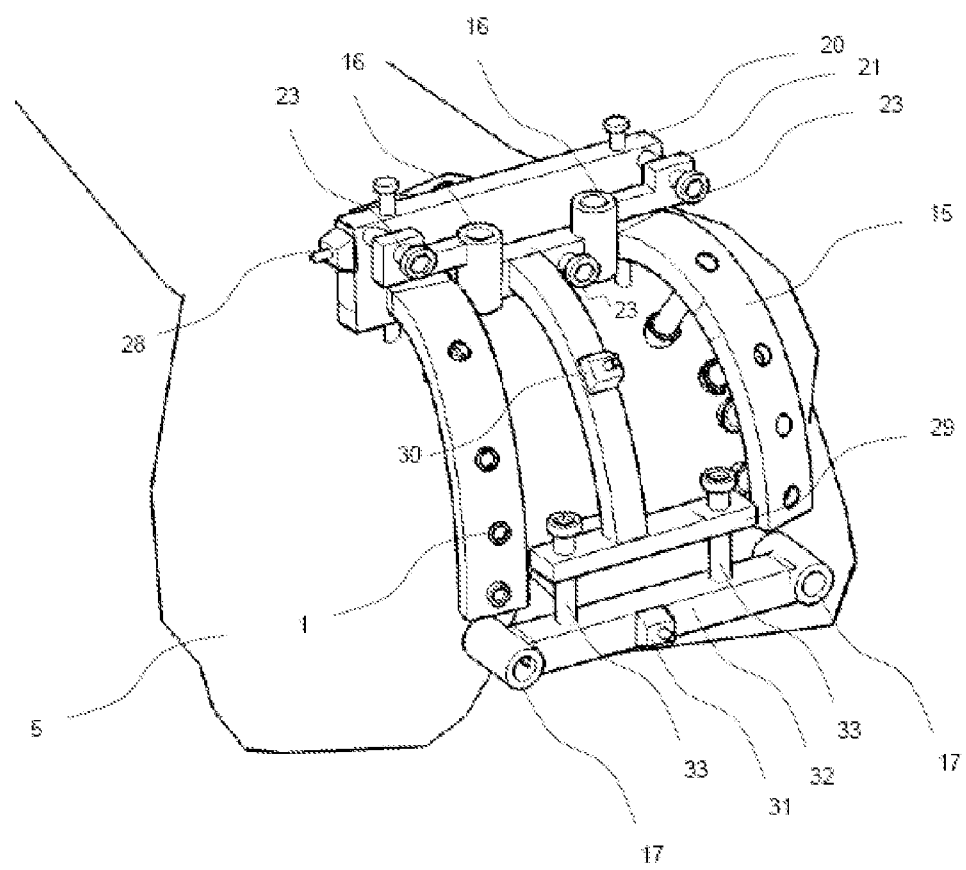
FIG. 9 is an oblique view of the adjustable guide with a fixed part and two dependent adjustable parts.

In another preferred embodiment, part C is attached to part B instead of part A such that the pair of holes of part B and the pair of holes of part C maintain their orthogonal relationship. In that case, the relationship between B and C is adjusted by only two screws. This design is detailed in FIG. 9. The part 21 that contains the distal holes 16 is adjusted with the three screws 23 as described above. Then, part 29 which contains the holes 17 is rigidly attached to 21 such that the holes 16 and 17 remain orthogonal. The two screws 33 are used to adjust the position of the part 32 that contains the holes 17, which represent mainly the rotation and antero-posterior adjustments of the femoral implant. A navigation tracker mounted on the fixation 31 is continuously tracked with respect to a reference tracker mounted on 30 until the parameters are adjusted to the desired positions. The geometrical relationships between the tracker fixations 28, 30, 31 are known by pre-calibration. In such design, part A is 15, part B is 21 and part C is 32.

In another embodiment, part B is rigidly fixed to the bone by screws or pins and the other parts A and C can be disassembled from B. Part A contains the pair of holes of the distal cutting guide. The tracker of the navigation system is attached or detached in a reproducible manner to part B for any further measurements that are necessary without having the adjustable guides in situ since they can be cumbersome. In that solution, the contact screws of part A may have to be removed or put to their zero position in order to avoid preventing adjustments of part C. It must be understood in that solution that the use of part A is only valid at first if the check performed with the navigation system is correct and if the surgeon does not want to modify parameters. It is also useful to preposition the blocks in an initial position close to the final position so that only minor adjustments are necessary which saves time but also reduces the needs for extensive lengths of adjustments which increase the size of the design.

All steps of the invention method can be performed in parallel for managing several implants, for instance femoral, tibial and patella implants for knee surgery.

Many different designs can be adjusted for applications of the method and extension of the device to other bone cuts such as tibia for instance.

It is also possible to reverse the importance of intra-operative navigation and the importance of CT or MR images by considering the device primarily for easy and fast navigation with the optional use of CT or MR images only for refining the planning strategy. In a preferred embodiment, the basis of the adjustable guide 15 is fixed to the bone with pins before the navigation landmarks are acquired. And a conventional navigation procedure can then be performed. In addition, surface points can be acquired on the bone surface in the coordinate system of a tracker mounted on the adjustable guide and those surface points can be registered with the CT or MR images using conventional surface matching techniques of navigation. It provides a registration between the adjustable block 15 and the CT or MR images, such that the planning of the implants can be immediately determined and visualized on the CT and MR images in addition to the navigation points and surfaces.

Advantages of the Invention

The advantage of the invention is to propose a process for saving time and increasing accuracy during orthopaedic procedures without the drawbacks of patient-specific guides and without the drawbacks of surgical navigation.

A straightforward combination of patient specific guides based on CT or MR images and navigation would simply consist in producing disposable patient specific guides using rapid machining preoperatively and then using a navigation system to check the correct location of the guide, which normally necessitates fixing additional pins to the bone for tracker fixation. But that would add complexity, cost and additional time to using one or the other solution.

The invention does not require to add additional pins compared to conventional procedures The invention does not necessitate to generate a single use patient specific guide which adds cost and logistics issues The invention makes it possible to use the planning made on the CT and MR images as a reference but also to adjust the optimal position of the implant intra-operatively to take into account data acquired intra-operatively.

The invention claimed is:

1. A surgical device, for the purpose of adjusting one or more cutting blocks to a desired position with respect to a bone of a patient, the device comprising:
   an adjustable guide with at least six adjustable screws whose length is calculated to create a contact point when the adjustable guide is in a desired position planned on preoperative CT or MR images,
   wherein the adjustable guide comprises two pairs of holes capable of guiding pins which position and fix said cutting blocks,
   a dedicated screwdriver to adjust the position of each screw to a target value,
   a navigation system operable to check a correct position of the adjustable guide with respect to one or more anatomical points.

2. A surgical device, for the purpose of adjusting one or more cutting blocks to a desired position with respect to a bone of a patient, the device comprising:
   an adjustable guide with at least six adjustable screws whose length is calculated to create a contact point when the adjustable guide is in a desired position planned on preoperative CT or MR images,
wherein the adjustable guide comprises one cutting block and one pair of holes capable of guiding one or more pins which position and fix a cutting block,
   a dedicated screwdriver to adjust a position of each screw to a target value,
   a navigation system operable to check a correct position of the adjustable guide with respect to one or more anatomical points.

3. The device of claim 1, wherein the adjustable guide is connected to two cutting blocks or pairs of holes with three adjustable screws.

4. The device of claim 1, wherein the adjustable guide is connected to one cutting block or pair of holes with three adjustable screws and the cutting block or pair of holes is connected to a pair of holes with two adjustable screws.

5. The device of claim 1, wherein the dedicated screwdriver comprises a motor and a computer for controlling the motor to adjust the length of each screw automatically to a target position.

6. A method of adjusting one or more cutting blocks to a desired position with respect to a bone of a patient, said method comprising:
   (1) acquiring one or more CT or MR images and planning an implant position responsive to said images;
   (2) extracting one or more bone and/or cartilage surfaces from said images;

(3) calculating one or more screw lengths contained in an adjustable guide for said cutting blocks, said adjustable guide having at least six adjustable screws, such that the adjustable guide is in a desired position when the screws are in contact with the bone and/or cartilage surface;

(4) adjusting the screws of the adjustable guide to a target position using a dedicated screwdriver prior to incising the patient;

(5) positioning the adjustable guide in contact with the bone and/or cartilage surface, attaching a navigation tracker to the adjustable guide, the tracker having a known relationship with respect to the adjustable guide, and operating a navigation system responsive to a position of the tracker to check that the adjustable guide is in a correct position with respect to one or more anatomical points or with respect to additional patient data collected intra-operatively; and (6) iterating steps (3) and/or (4) until condition of step (5) is met.

7. The device of claim 1, wherein the anatomical points are acquired from one or more intra-operative CT or MR images of the patient including the anatomical points, and the anatomical points are registered with a position of the adjustable block.

8. The device of claim 2, wherein the adjustable guide is connected to two cutting blocks or pairs of holes with three adjustable screws.

9. The device of claim 2, wherein the adjustable guide is connected to one cutting block or pair of holes with three adjustable screws and the cutting block or pair of holes is connected to a pair of holes with two adjustable screws.

10. The device of claim 2, wherein the dedicated screwdriver comprises a motor and a computer for controlling the motor to adjust the length of each screw automatically to a target position.

11. The device of claim 2, wherein the anatomical points are acquired from one or more intra-operative CT or MR images of the patient including the anatomical points, and the anatomical points are registered with a position of the adjustable block.

12. The device of claim 1, wherein the adjustable guide has more than twelve adjustable screws.

13. The device of claim 2, wherein the adjustable guide has more than twelve adjustable screws.

14. The method of claim 6, wherein step (5) comprises determining at least one reference anatomical point in a coordinate system of the adjustable guide from kinematics of the patient's bone.

15. The method of claim 6, wherein step (5) comprises digitizing at least one reference anatomical point with a navigation pointer.

* * * * *